United States Patent [19]

Wincheski et al.

[11] Patent Number: 5,493,511
[45] Date of Patent: Feb. 20, 1996

[54] HIGH SPEED THIN PLATE FATIGUE CRACK MONITOR

[75] Inventors: Buzz A. Wincheski; Joseph S. Heyman, both of Williamsburg; Min Namkung, Yorktown; James P. Fulton, Hampton, all of Va.

[73] Assignee: Administrator, National Aeronautics and Space Administration, Washington, D.C.

[21] Appl. No.: 988,084

[22] Filed: Dec. 8, 1992

[51] Int. Cl.⁶ .................................................. G01H 11/00
[52] U.S. Cl. .......................... 364/508; 364/506; 364/507; 73/577; 73/799; 73/801; 73/668
[58] Field of Search .................................. 364/507, 508, 364/506, 505, 512; 73/579, 583, 577, 799, 801, 802, 812, 668, 587, 588, 584, 586, 570, 576, 578, 589, 606, 786; 324/718

[56] References Cited

U.S. PATENT DOCUMENTS

| 3,830,099 | 8/1974 | Ichikawa | 73/668 |
|---|---|---|---|
| 3,850,028 | 11/1974 | Thompson et al. | 73/643 |
| 4,048,847 | 9/1977 | Alers et al. | 73/812 |
| 4,063,282 | 12/1977 | Exton | 358/106 |
| 4,188,830 | 2/1980 | Mason et al. | 73/801 |
| 4,390,262 | 6/1983 | Hirohata et al. | 354/230 |
| 4,751,657 | 6/1988 | Imam et al. | 73/577 |
| 4,912,411 | 3/1990 | Allison et al. | 73/801 |
| 4,975,855 | 12/1990 | Miller et al. | 364/507 |
| 5,069,800 | 11/1991 | Brook et al. | 364/507 |
| 5,079,955 | 1/1992 | Eberhardt | 73/799 |
| 5,195,046 | 3/1993 | Gerardi et al. | 73/583 |
| 5,216,921 | 6/1993 | Tsuboi | 73/579 |
| 5,351,543 | 10/1994 | Migliori et al. | 73/579 |

FOREIGN PATENT DOCUMENTS

| 0031637 | 3/1981 | Japan | 73/576 |
|---|---|---|---|
| 0212562 | 9/1987 | Japan | 73/588 |
| 1154606 | 5/1985 | U.S.S.R. | 73/576 |
| 2202630 | 9/1988 | United Kingdom | 73/801 |
| 2217521 | 10/1989 | United Kingdom | 73/668 |

OTHER PUBLICATIONS

W. Weaver, Jr. et al. "Vibrational analysis", Finite Elements for Structural Analysis, Prentice–Hall, Inc., Englewood Cliffs, N.J., 1984.

F. Hamel et al. "Detection of crack propagation in fatigue with acoustic emission", Strength of Metals and Alloys, R. C. Gifkins, ed., Proceedings of the 6th International Conference, Melbourne, Australia, vol. 2, Pergamon Press, 1982, pp. 839–844.

Primary Examiner—Emanuel T. Voeltz
Assistant Examiner—Hal P. Wachsmann
Attorney, Agent, or Firm—George F. Helfrich; Robin W. Edwards

[57] ABSTRACT

A device and method are provided which non-destructively detect crack length and crack geometry in thin metallic plates. A non-contacting vibration apparatus produces resonant vibrations without introducing extraneous noise. Resulting resonant vibration shifts in cracked plates are correlated to known crack length in plates with similar resonant vibration shifts. In addition, acoustic emissions of cracks at resonance frequencies are correlated to acoustic emissions from known crack geometries.

25 Claims, 11 Drawing Sheets

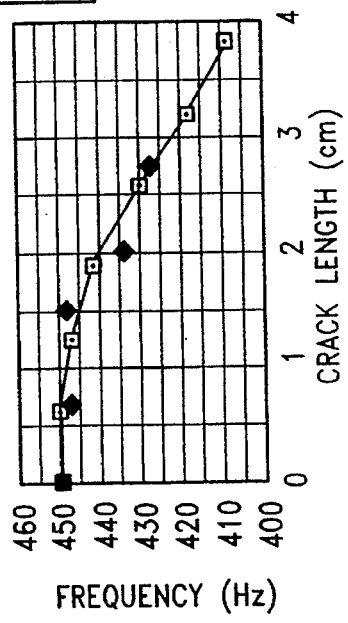
FIG. 15
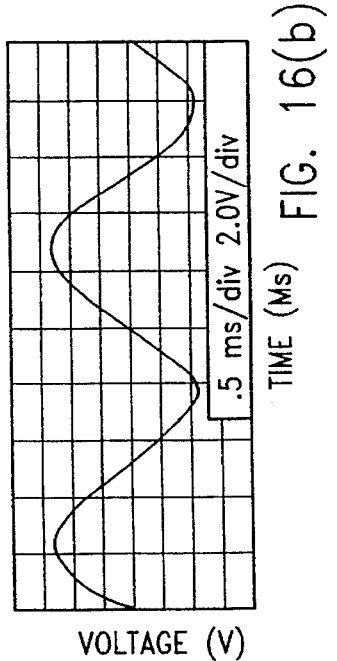
FIG. 16(a)
FIG. 16(b)
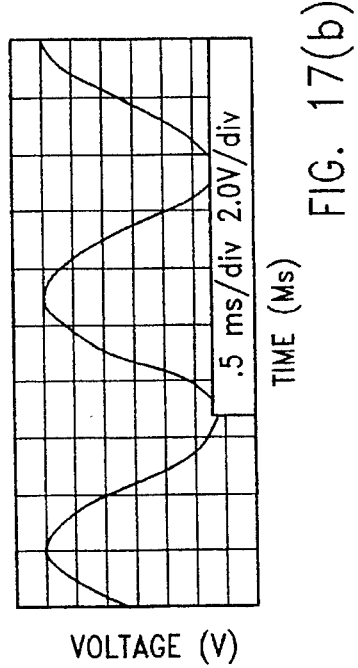
FIG. 17(a)
FIG. 17(b)

HIGH SPEED THIN PLATE FATIGUE CRACK MONITOR

ORIGIN OF THE INVENTION

The invention described herein was jointly made in the performance of work under a NASA contract and an employee of the United States Government. In accordance with 35 U.S.C. 202, the contractor elected not to retain title.

BACKGROUND OF THE INVENTION

1. Technical Field of the Invention

The present invention relates generally to the detection of cracks and more particularly to the nondestructive detection and characterization of cracks.

2. Discussion of the Related Art

The rapid detection and characterization of fatigue cracks are of major importance for many critical structures. Recent developments in the airline industry have initiated a rethinking of conventional nondestructive evaluation (NDE) methods. As the commercial airline fleet continues to age, the NDE community is being challenged to develop rapid nondestructive testing techniques which can ensure the structural integrity of aging aircraft while keeping aircraft down time to a minimum.

Present methods of fatigue crack detection include eddy current, ultrasonic, dye penetrant, magnetic particle, and acoustic emission (AE) testing. Eddy current, ultrasonic, dye penetrant and magnetic particle testing are all localized techniques, that is, only a small area of the structure is examined at a time. In addition, the dye penetrant technique requires a paint free surface. Both ultrasonic and dye penetrant testing depend upon the application of foreign substances to the surface of the specimen which allows for possible contamination. All of the present techniques also depend heavily on the inspector, requiring a skilled operator in order to be effective. Acoustic emission testing has the advantage of being able to monitor large structures, but yields difficult to interpret results. It has been most successfully used in the past to monitor crack growth. See C. B. Scruby, *Quantitative Acoustic Emission Techniques*, AERE R 11202, July 1984.

U.S. Pat. No. 4,975,855 to Miller et al. discloses comparing the natural frequency responses of a vibrational shaft to an analytical model to determine crack presence and severity, i.e., to perform modal analysis. Particularly, FIG. 9 of this patent shows that as the severity of the crack increases, the natural frequency splits and the difference between the two new frequencies increases. The shaft is vibrated by a directly contacting shaker which induces extraneous frequencies which would complicate any attempt to combine this system with an acoustic emission crack detection system. U.S. Pat. No. 4,188,830 to Mason et al. discloses measuring acoustic emission emitted from opposite crack faces rubbing against each other as the structure is vibrated. Once again, a direct contact vibrator is used, thereby complicating signal analysis by introducing extraneous signals.

In conventional acoustic emission techniques, it is difficult to obtain stress information at the time of emission events under passive loading conditions. Such conventional techniques require a separate sensor technique to determine the stress as a function of time. Although static or linear loading techniques can produce a record of stress versus the acoustic emission event, such techniques have the drawback of requiring further damage to the sample in the form of crack growth or micro-growth as a source of the emission event.

OBJECTS

It is accordingly an object of the present invention to nondestructively detect the presence of cracks in a structure.

It is another object of the present invention to nondestructively characterize the length and nature of cracks in a structure.

It is a further object of the present invention to detect and characterize cracks with a technique that is not localized.

It is another object of the present invention to detect and characterize cracks in a specimen without contaminating the surface with foreign substances such as ultrasonic couplants or penetrating dyes.

It is another object of the present invention to detect and characterize cracks in a specimen in a relatively straightforward, easily interpreted manner.

It is a further object of the present invention to detect and characterize cracks in a specimen without requiring significant operator interpretational skills.

It is another object of the present invention to detect and characterize cracks with a technique that uses a non-contacting source of vibration.

It is a further object of the present invention to nondestructively detect and characterize cracks in a specimen without requiring access to both surfaces of the specimen.

SUMMARY OF THE INVENTION

It is a primary object of the present invention to nondestructively detect and characterize cracks in thin metallic plates. Additional objects and advantages of the present invention are apparent from the specifications and drawings which follow.

The foregoing objects are achieved by vibrating the test plate at its resonance frequency by using a non-contacting vibrating apparatus. Crack lengths in the test plate are then determined by correlating resonance frequencies for test plates to resonance frequencies for uncracked plates and plates with known crack lengths. Additional information concerning the nature of the cracks can be determined by recording variations in the acoustic emission waveforms produced at the resonance frequency of the test plate as a result of crack face interactions.

Use of resonance frequencies coupled with acoustic emission permits accurate determinations of the length and character of cracks without requiring further crack growth in the test plate. In addition, use of a non-contacting vibration apparatus prevents the introduction of extraneous noise into the test plate and permits rapid evaluation of test samples in the field.

BRIEF DESCRIPTION OF THE DRAWINGS

FIG. 9b depicts the driving function for the acoustic emission waveform of FIG. 9a.

FIG. 10b depicts the driving function for the acoustic emission waveform of FIG. 10a.

FIG. 11b depicts the driving function for the acoustic emission waveform of FIG. 11a.

FIG. 15 illustrates the correlation between finite element and experimental data for frequency as a function of crack length.

FIG. 16a depicts the acoustic emission waveform captured at the resonance frequency of the second vibrational plate mode for a plate with a 2.8 cm. crack using a PVDF transducer.

FIG. 16b depicts the driving function for the acoustic emission waveform of FIG. 16a.

FIG. 17a depicts the acoustic emission waveform captured at the resonance frequency of the second vibrational plate mode for an uncracked plate, using a PVDF transducer.

FIG. 17b depicts the driving function for the acoustic emission waveform of FIG. 17a.

DETAILED DESCRIPTION OF THE INVENTION

Figure 1:
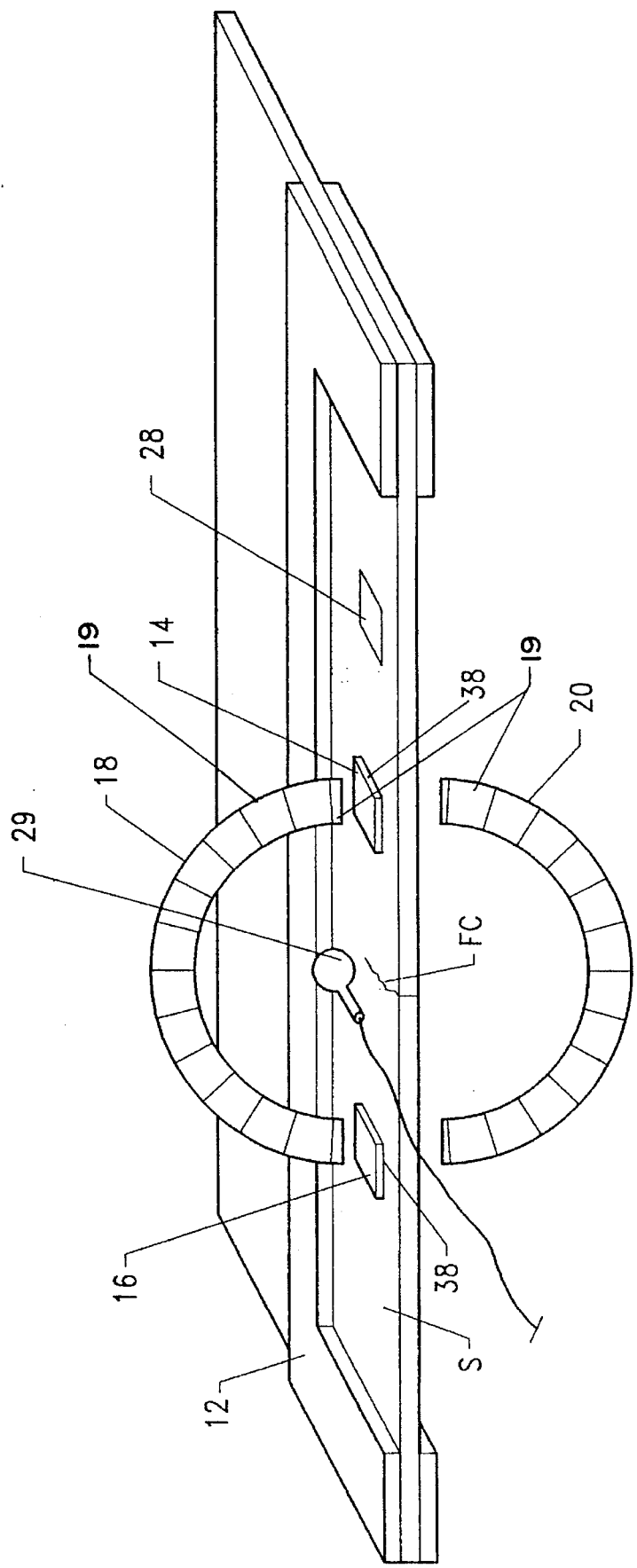
FIG. 1 is a schematic representation of the present invention as used to test thin plates.

An embodiment of an apparatus for detecting and characterizing cracks according to the present invention is shown in FIG. 1. Such an apparatus and method have a variety of important applications including the study of aging aircraft discussed in the Background section. As a part of the effort to meet these needs, low frequency resonant modal analysis is being explored as a means of fatigue crack detection and characterization in airframe structures.

Modal analysis is based on the excitation of free standing vibrational waves in a structure. The presence of structural defects alters both the shape of the modal patterns and the resonance frequency at which the modes will stand. The vibrational status of the structure can be predicted using a finite element approach so that the inversion of the acquired data is a less formidable task than for other NDE techniques.

To determine crack length, a test plate is vibrated using a non-contacting apparatus. The vibration apparatus consists of rare earth permanent magnets attached to the surface of the test sample and an electromagnet positioned over the rare earth magnets at some distance from the sample surface. An alternate embodiment of the vibration apparatus uses a ferrite-core electromagnet with rare earth permanent magnets attached at each end. This assembly is positiond at some distance from the sample surface. The resonance frequency of the test plate is determined by tracking the peak output voltage from a transducer attached to the sample surface. The crack length in the sample is then determined by correlating the resonance frequency in the test sample to the resonance frequency determined for plates of similar size and composition containing cracks of known length.

To determine crack geometries, the test sample is vibrated at the resonance frequency and the acoustic emissions produced by the interactions of crack faces are detected. These acoustic emissions are correlated to acoustic emissions determined for cracks with known geometries in thin plates of similar size and composition in order to determine crack geometries in the test sample.

Several inherent properties of low frequency resonant modal analysis lend themselves directly to the aging aircraft problem. First of all, resonant vibrations are relatively easy to produce in the thin aluminum alloys used for aircraft skins. Also, the technique provides information on the integrity of a structure over a large area and has potential to be relatively easily converted into a non-contact rapid scan instrument. Another advantage of the technique is the ability to predict responses from various structure/flaw combinations, using the finite element approach, so as to increase the confidence level of flaw detection while holding false calls to a minimum.

Tests were performed on aluminum alloy 2024-T3 sample plates S with dimensions of 12"×7"×0.040". The samples were notched in the center of the long edge and then cyclicly fatigued in order to induce fatigue crack growth by tension-tension loading at maximum and minimum amplitudes of 3000 lbs. and 500 lbs., respectively, at 15 Hz for 15,000 to 60,000 cycles. Four samples contained fatigue crack lengths of ⅛", ½", ⅞", and 1¾ respectively. A sample S with a slit of ⅞ as well as an unflawed sample were also included in the experiment. All flaws were grown from the center of the front edge of the sample and projected toward the rear edge. A clamped boundary was enforced along three sides of the sample S by a sample holder 12, leaving the cracked edge free to vibrate. The dimensions of the clamped portion of the plates were 10"×1¾".

Figure 2:
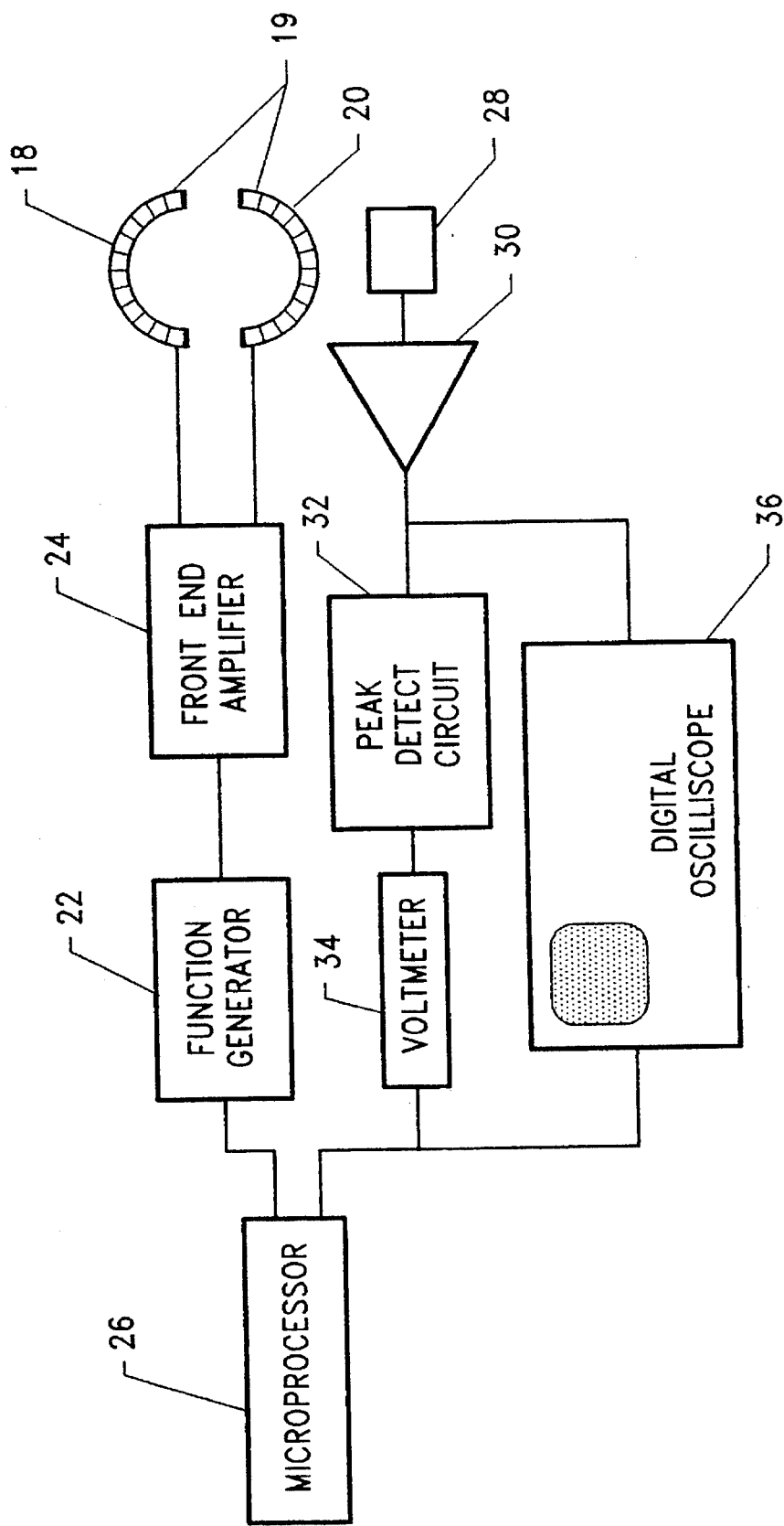
FIG. 2 is a block diagram depiction of the electronic equipment which controls sample vibration and records frequency and waveform.

In one embodiment shown in FIG. 1, rare earth permanent magnets 14 and 16 were attached directly to the sample S on either side of the fatigue crack FC. The magnets were placed ¼ back from the sample front edge and 1½ apart, centered along the centerline of the sample plate S. A sinusoidal mechanical driving force was applied to the samples through the use of U-shaped electromagnets 18 and 20 placed directly above and below the permanent magnets such that the oppositely charged poles of the electromagnets were aligned with each other and an associated permanent magnet along an axis. Common coil wire 19 is wrapped around each electromagnet in a different direction at each aligned axis. The poles of the permanent magnets 14 and 16 were aligned such that the force on opposite sides of the plate would be in opposite directions so that only even number modes, i.e., those with a minimum displacement along the centerline of the plate, would be excited. The driving current for the electromagnets 18 and 20 was supplied via common coil wire 19 by amplifying the output of a function generator 22 with a bipolar operational amplifier 24, as illustrated in FIG. 2. The frequency and amplitude of the driving signal were controlled by connecting the function generator 22 to a microprocessor 26. The microprocessor 26 is used to sweep the frequency of the function generator 22 over a given range, as discussed below in reference to FIG. 3, while keeping the amplitude constant at 3 volts. Accordingly, the plate and attached permanent magnets are "air-coupled" to the driving electromagnets, i.e., are driven by electromagnetic and not mechanical force. The plate is accordingly free from extraneous noise.

As the sample vibrates, stress waves will propagate to a polyvinyldene (PVDF) thin film transducer 28 attached to the sample and which outputs a voltage proportional to the amplitude of the stress waves. As discussed below, transducer 28 is also used to record the waveform of acoustic emission bursts to permit further flaw characterization. The transducer output is amplified by a large bandpass high gain amplifier 30 and then sent through a peak detect circuit 32 which tracks the peak transducer output. The output of circuit 32 is digitized by a voltmeter 34 which is read by the microprocessor 26. A table of the peak transducer output at each driving frequency of the electromagnetic is accordingly stored in computer memory. A digital oscilloscope 36 is used to monitor the waveform of the transducer output at the resonance frequency and the waveform is recorded with the microprocessor. Crack lengths in test plates are then determined by correlating the observed resonance frequency of the test plate to resonance frequencies for plates of similar size and composition containing known crack lengths. This correlation is preferably accomplished by the microprocessor.

It was found that a PVDF transducer 28 of dimensions 2.54 cm×2.54 cm with a 28 μm thickness could be attached directly to the sample surface without appreciably affecting the sample resonance frequency. At the resonance frequency of the plate a large increase in the amplitude of the plate vibration occurs. When the PVDF transducer is in direct contact with the sample surface, the amplitude of the plate vibrations will directly correlate to the voltage output of the transducer. Therefore the determination of resonance modes was accomplished by recording the peak amplitude of the transducer output as a function of the driving frequency of the electromagnets. A resonance mode would then be recorded as a peak in the amplitude vs. frequency data.

Figure 3:
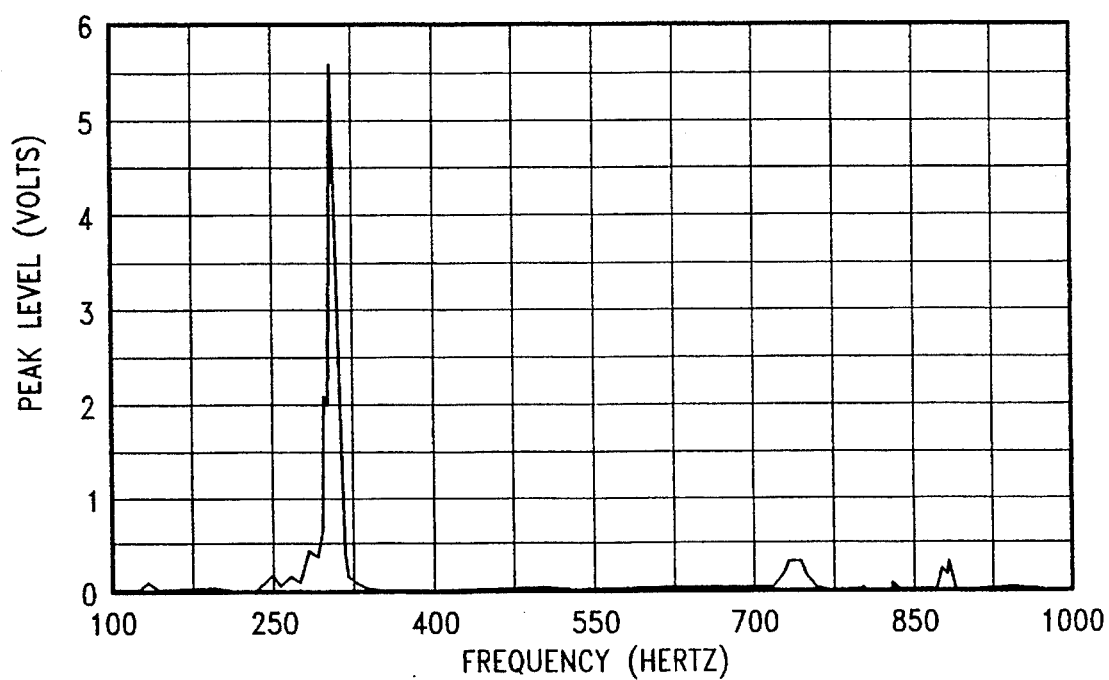
FIG. 3 is a plot illustrating the frequency of the second and fourth vibrational modes of a 0.040 in. thick 2024-T3 sample plate containing a ⅞ in. long fatigue crack.

For example, FIG. 3 shows typical experimental results of the procedure described above. The plot displays the data obtained for a plate containing a fatigue crack ⅞ long. The large peak in the transducer output at approximately 280–290 Hz signifies the frequency of the second vibrational plate mode for the sample. The graph in FIG. 3 also shows some indication of the fourth mode occurring near 725 Hz, although this experiment focused solely on tracking the location of the second mode. The data for FIG. 3 was acquired by rapidly stepping the driving frequency of the electromagnets 18 and 20 across the entire range of 100–1000 Hz in two Hz steps.

Figure 4:
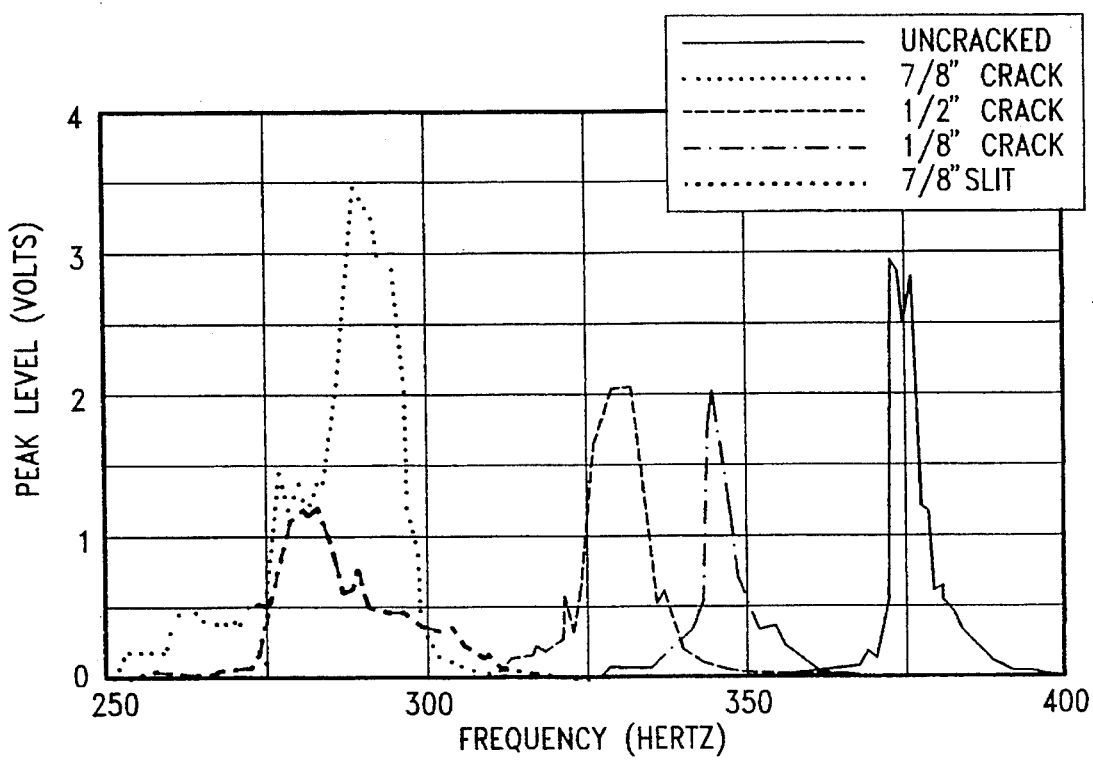
FIG. 4 is a plot illustrating the frequency shift of the second vibrational mode as a function of crack size.

Two procedures were employed to more accurately pinpoint the resonance frequency of the plates. Specifically, the range over which the frequency was scanned was limited to the area of interest for the second mode, and the current to the electromagnets was interrupted between each of the frequency shifts. FIG. 4 displays the results obtained when the two steps mentioned above are added to the experimental procedure. This plot combines the data obtained for test specimens on the same graph. The frequency shift caused by increasing the crack size is clearly visible in this figure, dropping from approximately 370 Hz for the uncracked plate to under 300 Hz for the plate with a fatigue crack ⅞" long, i.e., increasing flaw length reduces the frequency of the second plate vibrational mode. The graph also displays data obtained from a plate containing a slit of length ⅞". The close overlap of the peaks of the two data sets should be noted. The resonance frequency of these two different type flaws of the same length is nearly equal. This fact was used in developing the finite element model used to simulate the experimental conditions.

Figure 5:
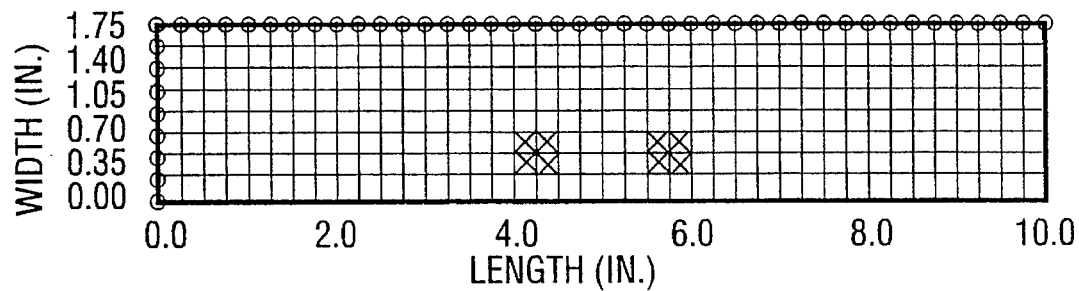
FIG. 5 is a drawing of the mesh used for finite element modeling of the uncracked plate.

The finite element model used in the computer simulations discussed immediately below was built entirely from first order quadrilateral plate elements. FIG. 5 displays the area discretization used to mesh the problem. The completed mesh for the uncracked plate contained 328 nodes and 280 elements. The clamped boundary conditions were enforced by holding the amplitude of all the degrees of freedom to zero for nodes lying along the edges of the mesh corresponding to the clamped sides and are represented by circled nodes. The permanent magnets 14 and 16 were added to the model by adjusting the mass of the elements over which the magnets were attached and are represented by the "X" hatching. Although this approach of handling the permanent magnets neglected any stiffness the magnets would add to the plate, it did account for all the mass of the system and allowed for the use of a simple two-dimensional model. The method incorporated for modeling the fatigue cracks took advantage of experimental results showing the similarity in resonance frequencies for plates with fatigue cracks as compared to plates with simple slits. The fatigue cracks were therefore modeled as zero width slits in the plate. The connectivity between adjacent quadrilateral elements was disconnected along the path the fatigue crack traversed, from the center of the front edge toward the rear edge. This modeling technique required only the use of additional nodes in the model. The number of elements was held constant and two-dimensional analysis could be used to solve the problem The COSMIC NASTRAN finite element software package was used to solve the eigenvalue equation for resonance mode determination. The NASTRAN package is available from the Computer Software Management and Information Center (COSMIC), Computer Services Annex, University of Georgia, Athens, Ga. 30602. NASTRAN uses a basic quadratic format in performing dynamic analysis. The quadratic equation governing the motion of a linear discretized system is $$[M]\{\ddot{u}\}+[B]\{\dot{u}\}+[K]\{u\}=P(t)\} \tag{1}$$

where [M] is the mass matrix, [B] is the damping matrix, [K] is the stiffness matrix, {P(t)} is the time dependent applied force vector, {u} is the vector of grid point displacements, and a dot denotes differentiation with respect to time. For the calculation of the natural frequencies of the plate, damping terms are neglected and the applied force vector is set to zero. As discussed in William Weaver, Jr. and P. R. Johnston, *Finite Elements for Structural Analysis*, Prentice-Hall, Inc., Englewood Cliffs, N.J., 1984, pp. 279–81. The equation of motion then reduces to $$[M]\{\ddot{u}\}+[K]\{u\}=\{0\} \quad (2)$$

It is next assumed that all parts of the system are vibrating sinusoidally with the same phase and frequency, such that $$\{u\}=\{\bar{u}\}\cos \omega t$$

(3)

$$\{\ddot{u}\}=\omega^2\{\bar{u}\}\cos\omega t \quad (4)$$

where $\{\ddot{u}\}$ represents the amplitudes of the degrees of freedom and $\omega$ is the circular frequency. Substituting equations (3) and (4) into equation (2) yields the linear eigenvalue equation $$([K]-\omega^2[M])\{\bar{u}\}=\{0\}) \quad (5)$$

Equation (5) is satisfied for the nontrivial case of nonzero $\{\bar{u}\}$ only when the determinant $([K]-\omega^2[M])$ vanishes. For each eigenvalue $\omega_i$ there corresponds an eigenvector $\{\bar{u}\}_i$ which is a natural mode of vibration of the plate.

Figure 6:
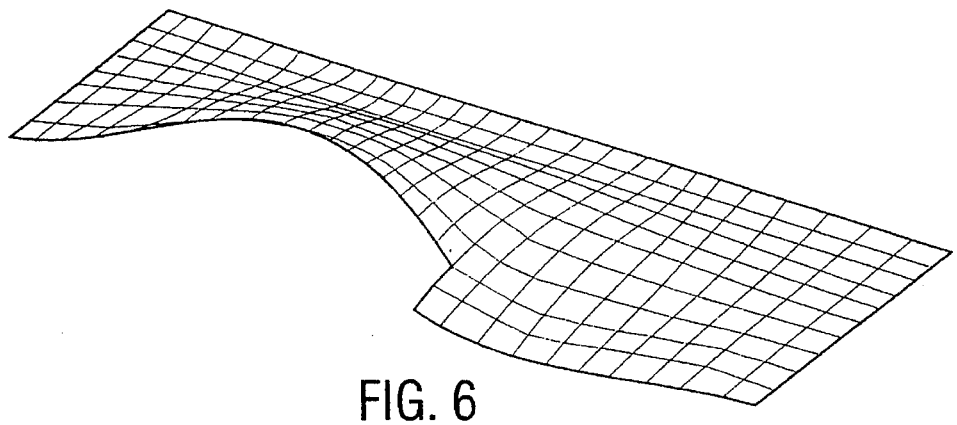
FIG. 6 depicts the finite element modeling results for a plate with a ¾ in. long fatigue crack.
Figure 7:
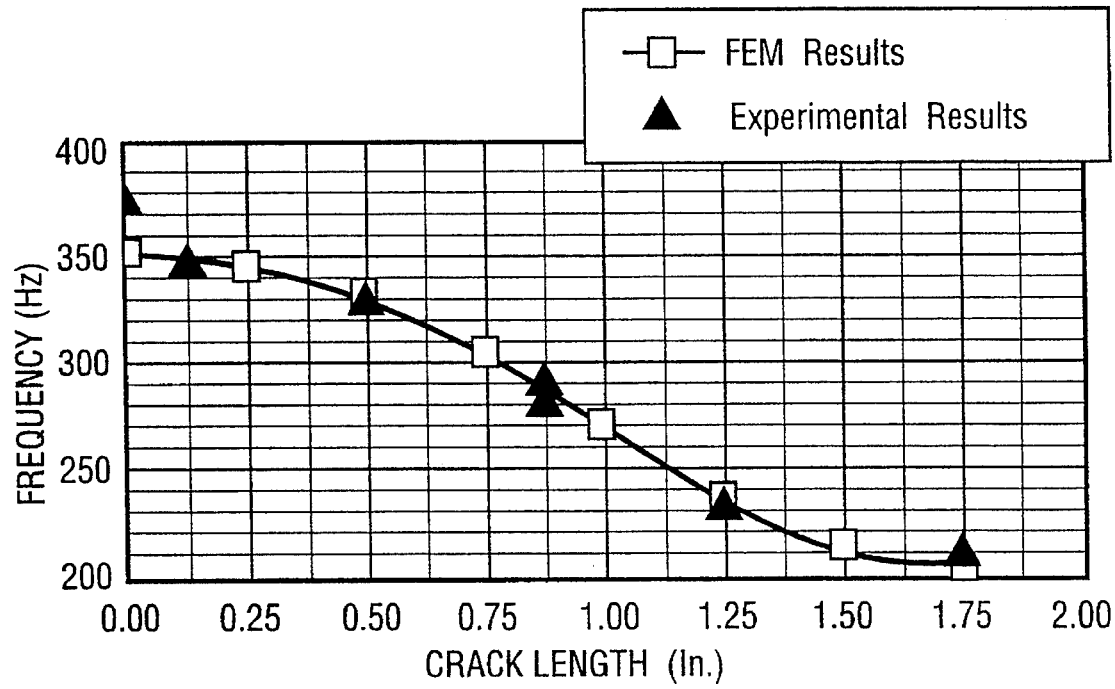
FIG. 7 is a plot of the frequency of the second vibrational mode as a function of crack length.

Finite element modeling results are displayed in FIG. 6 for a plate modeled with a ⅜ long fatigue crack. The frequency corresponding to the second vibrational mode is graphed in FIG. 7 as a function of defect size. This figure shows both modeling and actual experimental results. The close agreement between the results illustrates the effectiveness with which low frequency resonant modal analysis can characterize fatigue cracks in simple structures with well defined boundary conditions.

Figure 8:
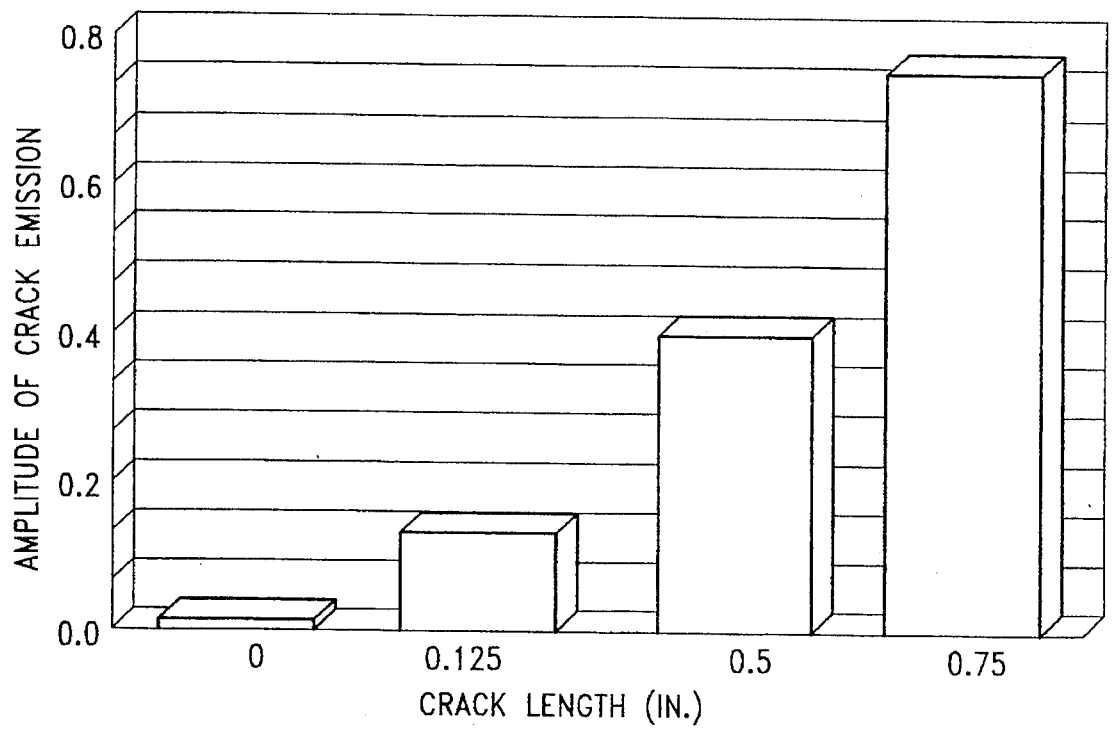
FIG. 8 is a bar graph illustrating the amplitude of crack emissions as a function of crack length.

Finite element modeling predicts the mechanical behavior of the test piece under vibration. For certain vibrational modes the faces of fatigue cracks present in the structure will interact. The interaction of the crack face walls releases energy into the sample which can be recorded with acoustic emission sensors. Emission events caused by crack wall interactions are identified by the frequency, amplitude, and phase of the signal with respect to that of the driving function on the plate. FIG. 8 displays the results of an emission waveform analysis. The amplitude of the high frequency stress waves associated with crack face rubbing increases as the crack length increases. A larger crack will develop a greater separation between crack face walls. This leads to a larger impact force between the crack faces and therefore a stronger output signal.

The acoustic emission (AE) signals emitted at the resonance frequency of the plates were next examined. The waveforms of the AE signals were captured by bypassing the peak detect circuitry 32 and the voltmeter 34 in favor of a digitizing oscilloscope 36 which monitored the acoustic emission signals, which were also recorded by the microprocessor 26. Initial results showed that a large portion of the signal being received by the transducer 28 was due to permanent magnet vibration on the sample surface. This noise was eliminated from the experiment by placing a thin piece of porous rubber 38 between the permanent magnets and the sample surface. This succeeded in eliminating the excess noise, but also caused a shift in all resonance frequencies since the stiffness of the system was changed. All acoustic emission waveform data was acquire at these shifted resonance frequencies for the second vibrational mode of the samples.

Figure 9A:
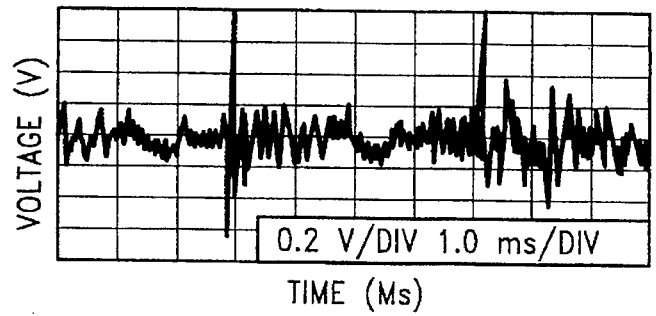
FIG. 9a depicts the acoustic emission waveform captured at the resonance frequency of the second vibrational plate mode for a plate containing a ⅞ in. fatigue crack.
Figure 9B:
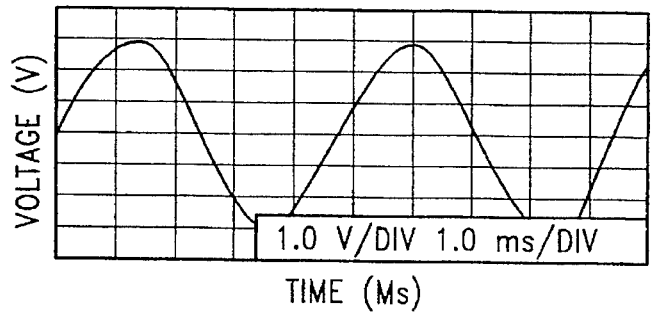
Figure 10B:
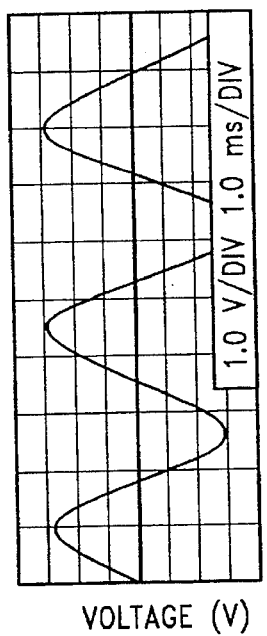
Figure 11B:
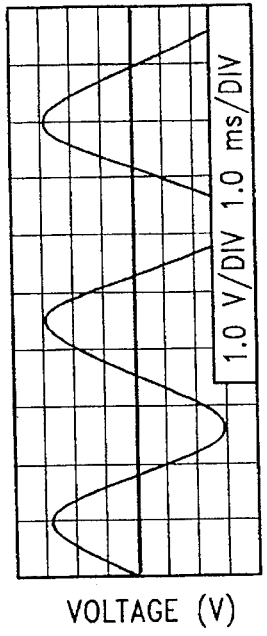
Figure 10A:
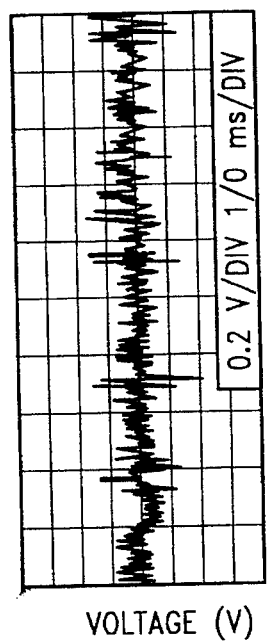
FIG. 10a depicts the acoustic emission waveform captured at the resonance frequency of the second vibrational plate mode for a plate containing a ½ in. fatigue crack.
Figure 11A:
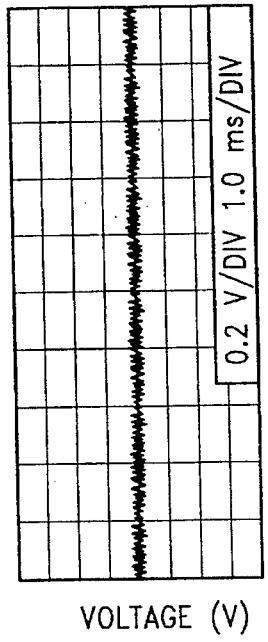
FIG. 11a depicts the acoustic emission waveform captured at the resonance frequency of the second vibrational plate mode for a plate with no cracks.

FIGS. 9(*a*), 10(*a*) and 11(*a*) display acoustic emission waveforms captured at the resonance frequency of the second vibrational plate mode for three different samples. The voltage-time plates relate directly to energy arrivals at the transducer surface. FIGS. 9(*b*), 10(*b*) and 11(*b*) are the respective driving functions for the acoustic emission waveforms of FIGS. 9(*a*), 10(*a*) and 11(*a*). FIG. 9(*a*) displays a large burst of high frequency energy occurring at a frequency equal to that of the driving force on the plate. This plate contained a relatively large fatigue crack with a length of ⅞". When the crack size was reduced to ½" a distinctively different emission waveform was recorded in FIG. 10(*a*) showing two emission events per cycle of the driving frequency. FIG. 11(*a*) displays the acoustic emission data captured for an uncracked plate, for which the high frequency acoustic emission bursts are completely absent.

The information contained in these plots, combined with knowledge gained from finite element modeling, can be used to develop a simple model of the interaction of crack face walls during vibration. A first approximation is given by the finite element crack model, approximating the crack as a thin slit. This choice is supported by the relationship between the modeled results and the experimentally determined resonance values, and the comparison between the experimentally determined resonance values for the two plates containing flaws of ⅞", one being a fatigue crack and the other being a thin slit.

Figure 12B:
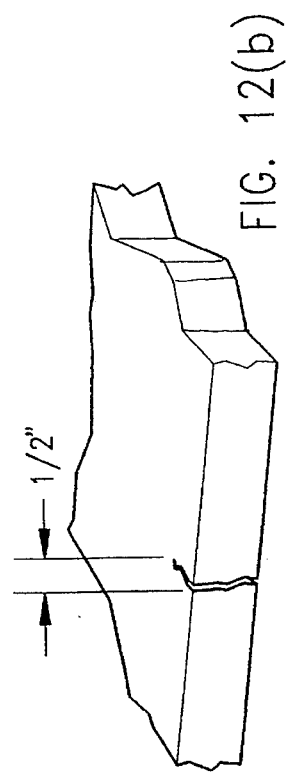
FIG. 12b is a schematic drawing of the cross section of a plate containing a linked ½ in. crack.
Figure 12A:
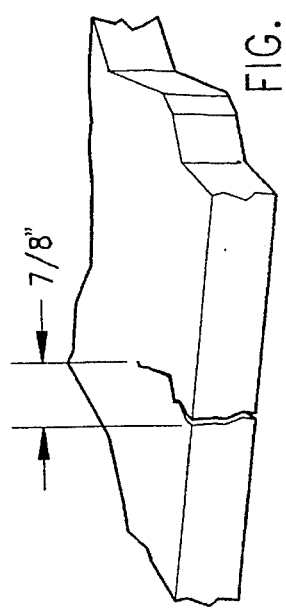
FIG. 12a is a schematic drawing of the cross section of a plate containing an unlinked ⅞ in. crack.

The thin slit model can be built upon from information contained in the voltage time plots of FIGS. 9(*a*), 10(*a*), and 11(*a*). Three distinctly different emission patterns are observed, those containing one, two, or zero high frequency bursts per cycle. One documented source of emission events is unsticking of cracks after closure. See F. Hamel and M. N. Bassim, "Detection of crack propagation in fatigue with acoustic emission," *Strength of Metals and Alloys*, R. C. Gifkines, ed., Pergamon Press, New york, 1983 pp. 839–44. In this experiment with the forcing function normal to the surface, examination of the AE signal will provide information concerning the crack cross-section perpendicular to the growth direction. Emission events will be recorded each time the crack faces interact and then separate. If one burst is recorded for each cycle of the driving frequency, it can be concluded that the crack face walls interact once per cycle. Two bursts will similarly signify two interactions per cycle. The crack face model corresponding to the recorded AE waveforms is shown in FIGS. 12(*a*) and 12(*b*). These figures depict crack cross-sections corresponding to different emission patterns. The cross-section of the large ⅞" crack of FIG. 12(*a*) will provide one AE burst per cycle, as no interaction will occur when the right-hand side of the crack is forced up and to left-hand side down. The smaller ½" crack of FIG. 12(*b*) is still linked so that two bursts per cycle will be recorded as the crack faces interact for both maximum and minimum amplitudes of each crack face. These geometries were confirmed by viewing the crack cross-sections with an optical microscope.

The present invention has the potential to detect local flaws while locking on a global scale. Low frequency resonant modal analysis combined with crack emission analysis potentially meets this challenge. The resonance frequency of a test piece with well defined boundary conditions has been found to directly correlate to localized flaws in the structure. In addition, an examination of the AE signal at the resonance frequency can provide characteristics of flaws presenting the structure. The ability to characterize a fatigue crack by its emission signature under resonant vibration has the potential to lead to a practical large area crack detection technique not limited by complex structural designs and boundary conditions.

The preceding discussion focused on edge cracks in a clamped sample. Fatigue cracks in the central region of aluminum alloy plates clamped on each edge were also examined. In addition, the effect of alternate sensors and the response at higher modes were studied. All tests were performed on aluminum alloy 6061-T6 plates with dimensions of 30.5 cm×12.7 cm×0.1 cm. A hole of radius 0.635 cm was drilled in the center of these plates. These holes were then notched on one or both sides before the samples were cyclically fatigued in order to induce fatigue crack growth. A sinusoidal loading cycle between upper and lower load values of approximately 3000 and 500 lbs. was used. Varying states of fatigue in the samples were induced by varying the number of cycles to which each sample was fatigued. Table 1 gives a breakdown of the loading parameters for each sample used in the study.

TABLE 1

LOADING PARAMETERS FOR EXPERIMENTAL SAMPLES

| Sample # | Sides Notched | # of Cycles | Fatigue Crack Length |
|---|---|---|---|
| 0 | 0 | 0 | 0 cm |
| 1 | 1 | 40,000 | 1.5 cm |
| 2 | 2 | 24,000 | 2.8 cm, 2.6 cm |
| 3 | 1 | 20,000 | 0.7 cm |
| 4 | 1 | 55,000 | 2.0 cm, 0.6 cm |
| 5 | 1 | 60,000 | 2.7 cm, 1.3 cm |

The fatigued samples were individually placed into the sample holder which supplied a clamped boundary along all edges of the plate. Rare earth permanent magnets were attached directly to the sample on either side of the fatigue crack. The spacing between the magnets was 3.8 cm, centered along the centerline of the plate. A sinusoidal mechanical driving force was applied to the samples via the electromagnets 18 and 26 placed directly above and below the permanent magnets 14 and 16. Microprocessor 26 was used to step the frequency of the forcing function over the range of interest, while recording the amplitude of the received signal at each frequency level. The poles of the permanent magnets were aligned such that the force on opposite sides of the plate would be in opposite directions. This alignment ensured the maximum shearing force across the fatigue crack face.

Various sensors were evaluated for retrieving information from the sample. Initial tests focused on the use of a polyvinylidene fluoride (PVDF) thin film transducer. Specifically, a PVDF transducer of dimensions 2.54 cm ×2.54 cm with a 28 μm thickness as in the foregoing example. For the present experimental setup however, this transducer was unable to consistently monitor the low frequency vibrations of the structure. Wide band commercial acoustic emission sensors were also tested, but produced no improvement in the results. The final pickup sensor that was used was an audible sound level meter 29 as shown in FIG. 1. This instrument gave an excellent recording of the low frequency resonant vibration, but was unable to detect high frequency signals associated with crack face rubbing during vibration which the PVDF thin film transducer could detect. A combination of these two pickup sensors was therefore used to monitor the vibrational status of the samples.

Air pressure vibrations received by the microphone of the sound level meter are converted into equivalent AC voltage vibrations. When the microphone is near the sample, surface vibrations of the sample will produce air pressure vibrations at the microphone head. At the resonance frequency of the plate a large increase in the amplitude of the plate vibrations occurs. Therefore the determination of resonance modes was accomplished by recording the peak amplitude of the sound level meter output as a function of the driving frequency of the electromagnets. A resonance mode would then be recorded as a peak in the amplitude vs. frequency data.

Figure 13:
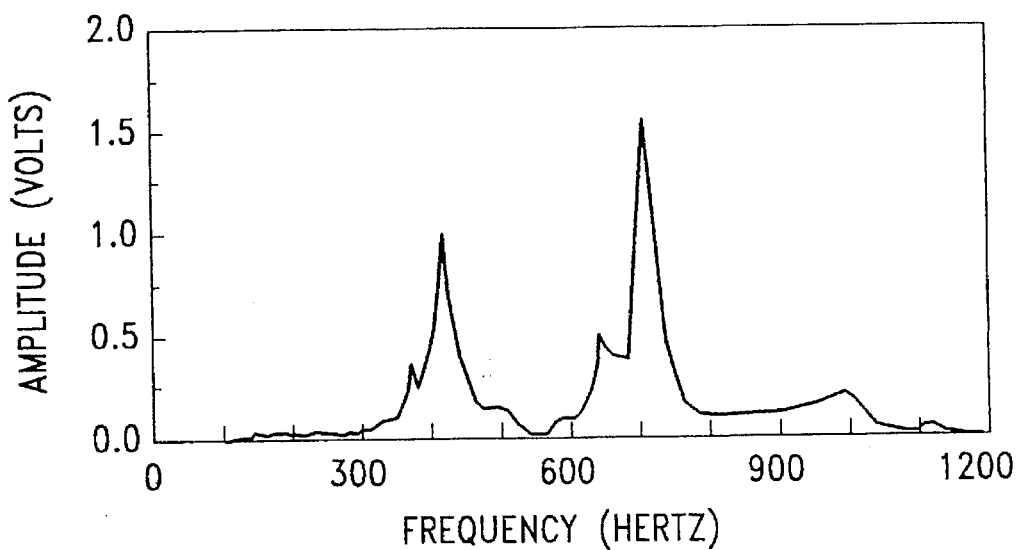
FIG. 13 is a plot of amplitude as a function of frequency for a 0.1 cm. thick plate containing a 2.7 cm. fatigue crack.
Figure 14:
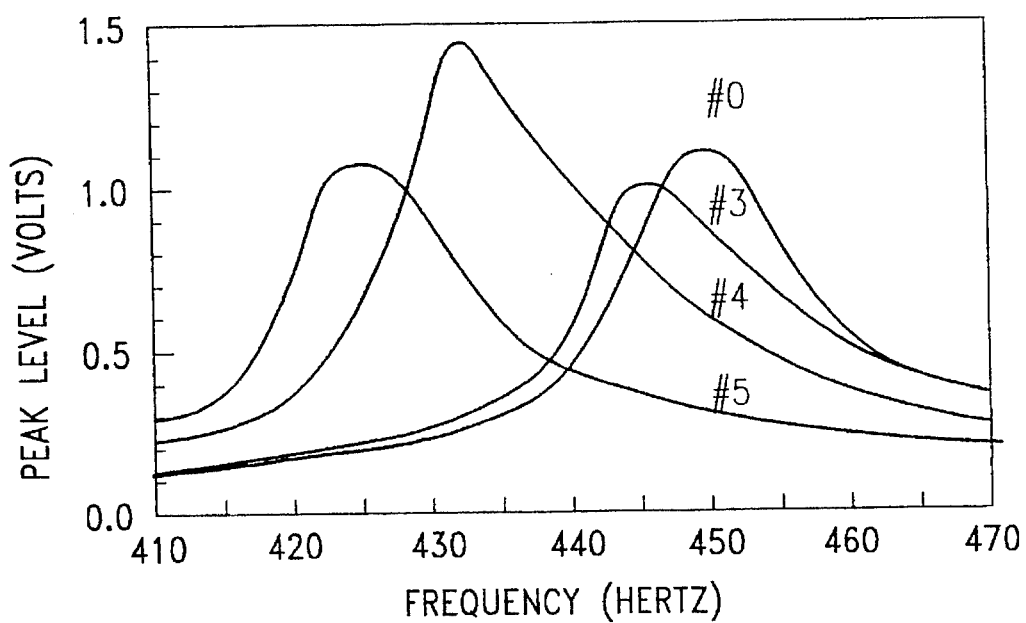
FIG. 14 is a plot of amplitude as a function of frequency for several samples of 0.1 cm. thick 6061-T6 plate.

FIG. 13 displays the experimental data acquired for sample 5 of Table 1. The directionality of the forcing function caused only even number modes to be stimulated so that the two sharp peaks in the graph locate the second and fourth resonance modes of the sample at approximately 430 Hz and approximately 750 Hz, respectively. FIG. 14 shows the results when the data from several samples are plotted on the same graph. The frequency scale for this figure has been reduced so as to focus on the second resonance mode in order to more clearly illuminate the frequency shift caused by fatigue cracks in the sample.

The finite element approach was used again to numerically calculate the mechanical response of the samples. A uniform mesh of first order elements was constructed for use in the COSMIC NASTRAN finite element package previously discussed. A two-dimensional analysis was used where fatigue cracks were modeled as zero width slits in the structure. FIG. 15 displays a comparison of finite element results and experimentally determined resonance values for the second plate vibrational mode. All of the experimental data in FIG. 15 are from plates that were notched on one side of the center hole. The corresponding crack length for these samples was therefore taken as the length of the crack propagating from the notched edge. Any crack growth from the opposite side of the center hole was ignored for the purposes of this figure. The finite element results shown in FIG. 13 are likewise results for fatigue cracks of the given lengths propagating from one side of the center hole.

A comparison of the finite element and experimental results showed a lower correlation at the fourth resonance mode than is seen in FIG. 15 for the second mode. This can be explained by the width of the resonance peaks as seen in FIG. 15. The width of the peak occurring at the fourth mode is much wider than that of the peak for the second mode. In addition, the normalized frequency shift of a given flaw does not increase at higher modes. Table 2 displays the normalized frequency shift generated by a 0.5 cm slit for the first nine resonance modes. This simulation data clearly shows that little advantage in terms of the normalized frequency shift can be obtained by working at a higher order mode.

TABLE 2

NORMALIZED FREQUENCY SHIFT FOR FIRST TEN RESONANCE MODES

| Mode # | Unflawed Resonance | 2.5 cm Slit Resonance | Normalized Shift |
|---|---|---|---|
| 1 | 393 Hz | 290 Hz | 1.0% |
| 2 | 450 Hz | 430 Hz | 4.4% |
| 3 | 717 Hz | 707 Hz | 1.4% |
| 4 | 781 Hz | 763 Hz | 2.3% |
| 5 | 1151 Hz | 1150 Hz | 0.1% |
| 6 | 1292 Hz | 1236 Hz | 4.3% |
| 7 | 1311 Hz | 1287 Hz | 1.8% |
| 8 | 1546 Hz | 1510 Hz | 2.3% |
| 9 | 1608 Hz | 1607 Hz | 0.1% |

It was previously mentioned that two different sensors were evaluated for use in this experiment, namely a sound level meter, from which the previous results were obtained, and a PVDF thin film transducer. The PVDF transducer, although unable to accurately trace the low frequency resonant vibrations, held a major advantage in its ability to detect high frequency noise associated with crack face rubbing during vibration. FIG. 16(a) is the signal obtained from the PVDF transducer for sample number 2 and FIG. 16(b) is the associated driving function. The large high frequency burst in the data obtained from sample number 2 is a result of fatigue crack face interaction during vibration. It is actually the unsticking of cracks after closure, which produces the acoustic signature seen in FIG. 16(a), as shown in F. Hamel and M. N. Bassiu, "Detection of crack propagation in fatigue with acoustic emission," *Strength of Metals and Alloys*, R. C. Gifkin, ed., Pergamon Press, N.Y., 1983. The sinusoidal force on the plate alternately pushes the crack face walls together and then begins to push them apart until the unsticking occurs, accompanied by a large burst of high frequency acoustic energy emission. FIG. 17(a) is he signal obtained by the PVDF transducer for uncracked sample number 0 and FIG. 17(b) is the associated driving force.

The present invention focuses on the detection of fatigue cracks in thin walled structures. The device also has the capability of detecting disbonds in layered structures and could be used to gain important information on crack propagation properties.

Figure 18:
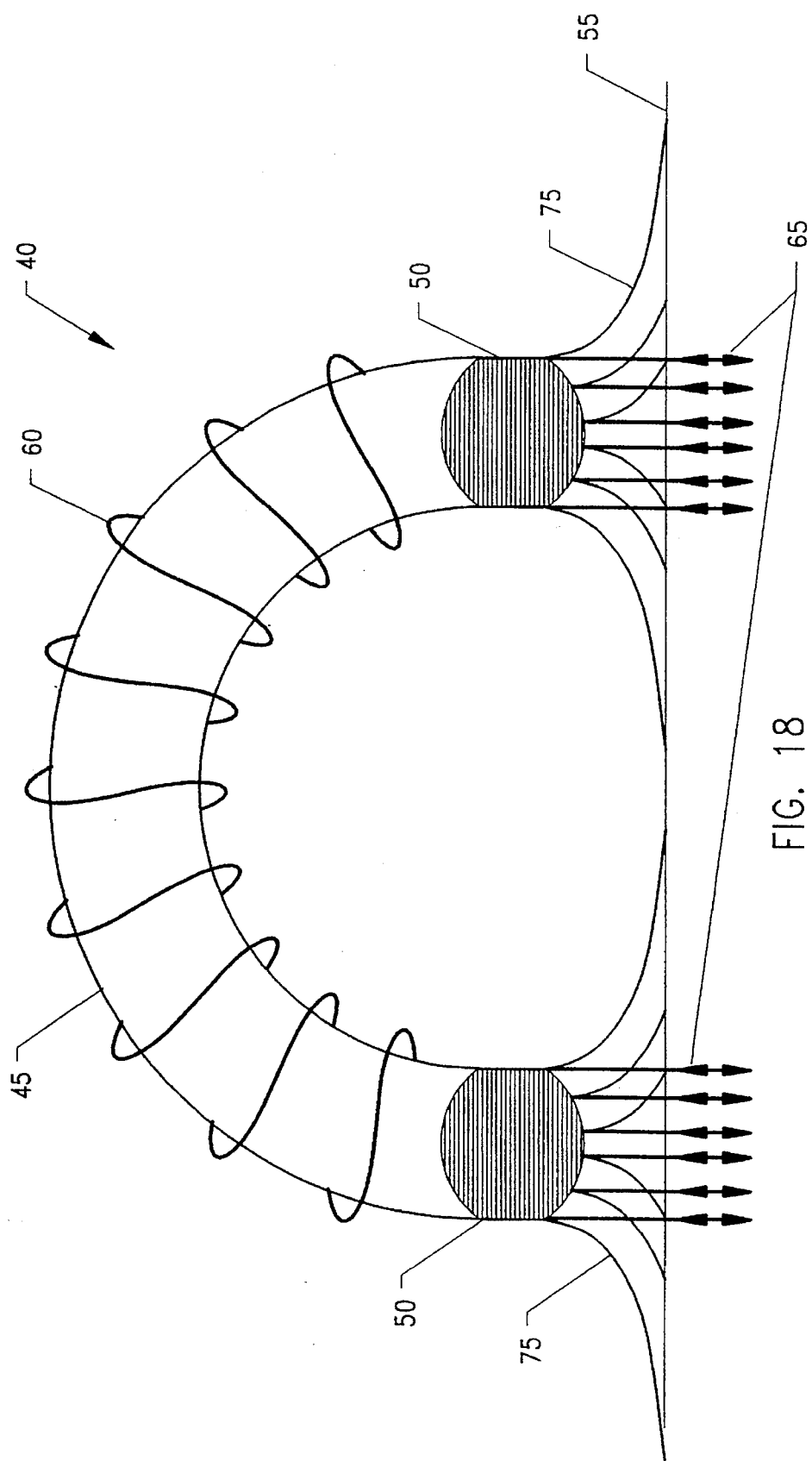
FIG. 18 is a schematic drawing of the nonconacting vibration device.
Figure 19:
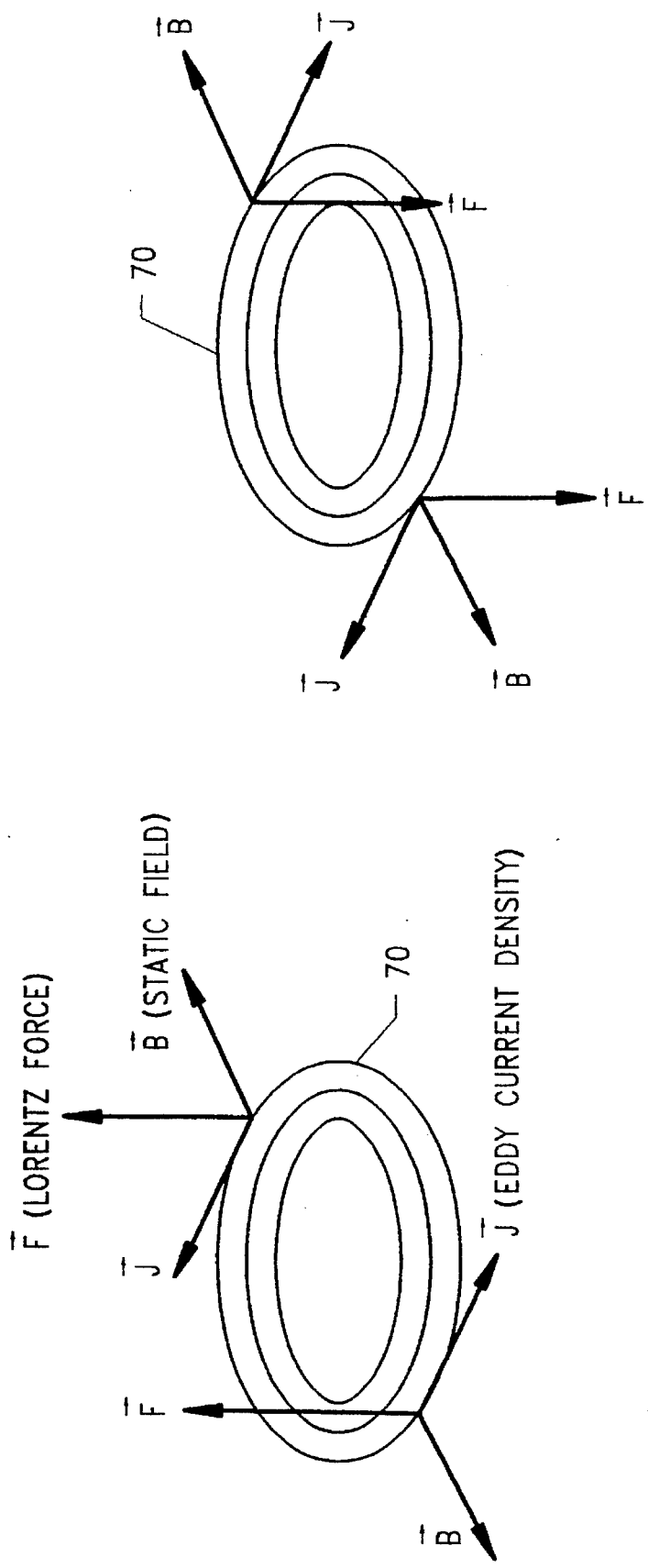
FIG. 19 depicts the induced eddy current and its interaction with the static magnetic fields.
Figure 20A:
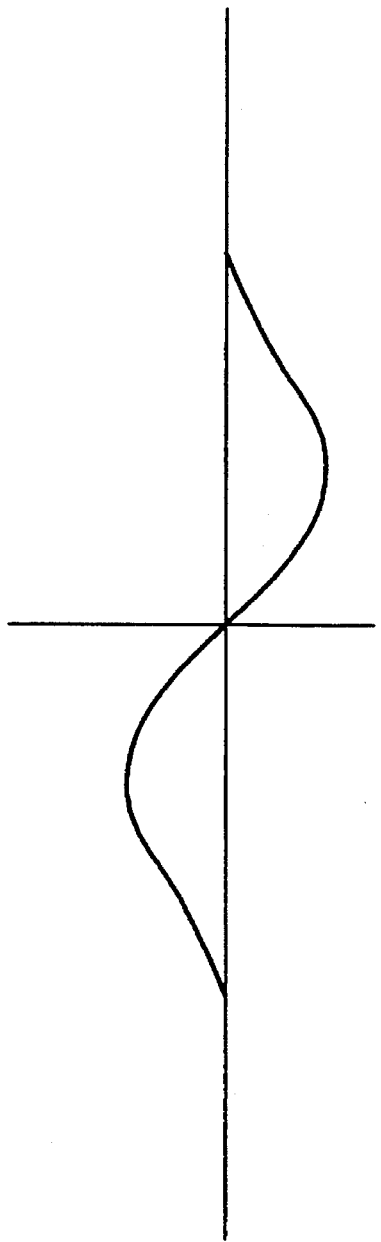
FIG. 20a a depicts one mode of local plate displacement.
Figure 20B:
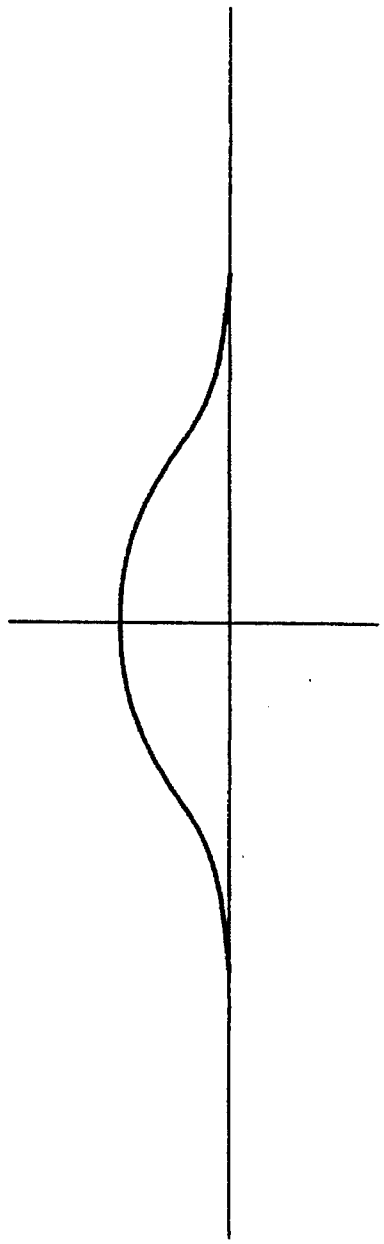
FIG. 20b depicts a second mode of local plate displacement.

An alternate embodiment of the invention does not require the permanent magnets 14 and 16 shown in FIG. 1. Instead, as shown in FIG. 18, the external vibration source 40 consists of a ferrite-core electromagnet 45 and a pair of rare earth permanent magnets 50, composed of a material such as cobalt-samarium. This embodiment uses a concentric distribution of electric currents which is induced by an AC magnetic field perpendicular to the test plate 55 in order to induce vibration in the plate 55. The ferrite-core electromagnet 45 has common coil wire 60 wrapped around the electromagnet and provides an AC magnetic field 65 with the field lines perpendicular to the plate surface 55. As illustrated in FIG. 19, such AC magnetic fields 65 create circular eddy currents 70 on the surface of a thin metal plate. The permanent magnets 50 provide static magnetic fields 75 which spread out rapidly such that the field lines B are mainly parallel to the plate surface 55. As illustrated in FIG. 19, the static field 75 exerts a force F which is a special case of the Lorentz force, on the electric current 70 in the direction perpendicular to the surface of the magnetic field B and eddy current J, which is the plate surface. By setting the polarity of the permanent magnets properly, the device can induce two different modes of local plate displacement as shown in FIGS. 20(a) and (b). For purposes of the present invention, the sinusoidal displacement mode shown in FIG. 20(a) is preferred.

The end surfaces of the electromagnet 45 are concave shaped to maintain uniform magnetic flux lines 65 in the region of the plate 55. The surfaces of the permanent magnets 50 are rounded to enhance the parallelism of the static magnetic fields 75 at the tip of the permanent magnets 50 and to ensure rapid spread of the static magnetic field lines 75. The optimized geometrical configurations of the electromagnet 45 and permanent magnets 50 is determined using finite element modeling techniques.

This alternate embodiment of a vibration source is particularly useful in the testing of hollow plate structures such as aircraft wings, where the interior of the wing cannot be accessed to attach permanent magnets as discussed in the first embodiment of FIG. 1. Since permanent magnets do not need to be attached to the surface of the test section, this embodiment provides a much faster method of crack detection. In addition, this noncontacting vibration source can be used to excite displacement modes for the application of other NDE techniques such as laser shearography and acoustic emission tests.

This invention provides a clear indication of fatigue cracks in the sample over a global scale. It is not limited to point by point testing like eddy current, ultrasonic, dye penetrant and magnetic particle techniques. Use of the non-contacting, sinusoidal driving mechanism of the present invention is unique in that all mechanical noise associated with the driver is removed from the system. The test piece, with magnets attached, is air coupled to the remainder of the driving circuitry, i.e., electromagnets, amplifier and function generator. This method eliminates extraneous noise associated with sample conditions. The present invention also produces a flaw signature which is reproducible and easy to interpret in terms of crack length and connectivity between crack face walls by monitoring both the frequency at which peak amplitude signals are obtained (modal analysis) and the waveform of the emitted signals (acoustic emission analysis).

Unlike conventional acoustic emission techniques, the present invention operates at the resonant frequency of the thin plate being tested and therefore does not require crack growth, which will further damage the sample. In conventional acoustic emission techniques, it is difficult to obtain stress information at the time of emission events under passive loading conditions. Such conventional techniques require a separate sensor technique to determine the stress as a function of time. Although static or linear loading techniques can produce a record of stress versus the acoustic emission event, such techniques have the drawback of requiring further damage to the sample in the form of crack growth or micro-growth as a source of the emission event. Since the main source of acoustic emission during resonant vibration is from crack face rubbing, crack growth during testing is avoided.

An important characteristic of using resonant vibration as a means of stimulating acoustic emission is that the stress distribution on the plate at the time of the emission burst can be determined from the phase of the emission bursts with respect to the driving function. This information is very important in determining the degree of closure or tightness of a fatigue crack. In addition, spurious signals due to background noise can be discriminated against since it is unlikely that they will repeatedly occur at the same frequency as the resonant vibrations. Emission events due to defects in the structure, however, will occur repeatedly at this frequency. Finally, resonance modal patterns can be modeled with a computer to allow accurate contemporaneous comparisons with test results.

Many modifications, substitutions, and improvement will be apparent to the skilled artisan without departing from the spirit and scope of the present invention as described herein and defined in the following claims.

We claim:

1. An apparatus for high speed monitoring of fatigue cracks in a thin plate, comprising:

means for vibrating to apply a sinusoidal driving function to produce resonant vibrations in said thin plate; and means for detecting acoustic emissions from cracks in said thin plate and correlating said acoustic emissions with crack geometry, wherein said acoustic emissions are produced by interactions of crack faces during resonant vibration of said thin plate.

2. The apparatus according to claim 1, wherein the means for detecting acoustic emissions comprises:

a transducer contacting said thin plate, wherein said transducer outputs voltages proportional to acoustic emissions resulting from crack face interactions; and a microprocessor for receiving the output voltages from said transducer and correlating said output voltages with crack geometry.

3. The apparatus according to claim 2, wherein the means for vibrating comprises:

a pair of permanent magnets to be attached to said thin plate whereby the area of said thin plate to be monitored lies between said pair of permanent magnets, the poles of each magnet aligned such that forces on opposite sides of said thin plate are in opposite directions;

two electromagnets, the first electromagnet to be located a distance directly above said permanent magnets, and the second electromagnet to be located a distance directly below said permanent magnets such that oppositely charged poles of said electromagnets align with each other and align with an associated permanent magnet along an axis;

means for supplying a driving current to said electromagnets; and means for controlling the frequency and amplitude of said driving current.

4. The apparatus according to claim 2 wherein the means for vibrating comprises:

an electromagnet having a first and second end, to be disposed at a distance from the surface of said thin plate, the ends of said electromagnet having a concave surface;

a pair of rare earth permanent magnets having a convex surface curvature, each of said rare earth permanent magnets to be fixedly disposed at each concave end of said electromagnet;

means for supplying a driving current to said electromagnet; and means for controlling the frequency and amplitude of said driving current.

5. The apparatus according to claim 1, wherein the means for vibrating comprises:

a pair of permanent magnets to be attached to said thin plate whereby the area of said thin plate to be monitored lies between said pair of permanent magnets, the poles of each magnet aligned such that forces on opposite sides of said thin plate are in opposite directions;

a pair of electromagnets, the first electromagnet to be located a distance directly above said permanent magnets, and the second electromagnet to be located a distance directly below said permanent magnets such that oppositely charged poles of said electromagnets align with each other and align with an associated permanent magnet along an axis;

means for supplying a driving current to said electromagnets; and means for controlling the frequency and amplitude of said driving current.

6. The apparatus according to claim 1 wherein the means for vibrating comprises:

an electromagnet having a first and second end, to be disposed at a distance from the surface of said thin plate, each of the first and second ends of said electromagnet having a concave surface;

a pair of rare earth permanent magnets having a convex surface curvature, each of said rare earth permanent magnets to be fixedly disposed at each concave end of said electromagnet;

means for supplying a driving current to said electromagnet; and means for controlling the frequency and amplitude of said driving current.

7. The apparatus according to claim 1 further comprising a means for detecting resonance frequencies of said thin plate.

8. The apparatus according to claim 7, wherein the means for detecting acoustic emissions comprises:

a transducer contacting said thin plate, wherein said transducer outputs voltages proportional to impact energies resulting from crack face interactions; and a microprocessor for receiving the outputs from said transducer and correlating said output with crack geometry.

9. The apparatus according to claim 8, wherein the means for vibrating comprises:

a pair of permanent magnets to be attached to said thin plate whereby the area of said thin plate to be monitored lies between said pair of permanent magnets, the poles of each magnet aligned such that forces on opposite sides of said thin plate are in opposite directions;

two electromagnets, the first electromagnet to be located a distance directly above said permanent magnets, and the second electromagnet to be located a distance directly below said permanent magnets such that oppositely charged poles of said electromagnets align with each other and align with an associated permanent magnet along an axis.

10. The apparatus according to claim 8 wherein the means for vibrating comprises:

an electromagnet having a first and a second end, to be disposed at a distance from the surface of said thin plate, the ends of said electromagnet having a concave surface;

a pair of rare earth permanent magnets having a convex surface curvature, each of said permanent magnets to be fixedly disposed at each concave end of said electromagnet;

means for supplying a driving current to said electromagnet; and means for controlling the frequency and amplitude of said driving current.

11. The apparatus according to claim 7, wherein the means for detecting resonance frequencies comprises:

a transducer contacting said thin plate whereby said transducer outputs voltages proportional to the amplitude of stress waves in said thin plate resulting from resonant vibrations;

a peak detect circuit for tracking the peak output voltages from said transducer; and a microprocessor for receiving and correlating the peak output voltages tracked by the peak detect circuit with crack length.

12. The apparatus according to claim 7, wherein the means for vibrating comprises:

a pair of permanent magnets to be attached to said thin plate whereby the area of said thin plate to be monitored lies between said pair of permanent magnets, the poles of each magnet aligned such that forces on opposite sides of said thin plate are in opposite directions;

two electromagnets, the first electromagnet to be located a distance directly above said permanent magnets, and the second electromagnet to be located a distance directly below said permanent magnets such that oppositely charged poles of said electromagnets align with each other and align with an associated permanent magnet along an axis;

means for supplying a driving current to said electromagnets; and means for controlling the frequency and amplitude of said driving current.

13. The apparatus according to claim 7 wherein the means for vibrating comprises:

an electromagnet having a first and second end, to be disposed at a distance from the surface of said thin plate, the ends of said electromagnet having a concave surface;

a pair of rare earth permanent magnets having a convex surface curvature, each of said rare earth permanent magnets to be fixedly disposed at each concave end of said electromagnet;

means for supplying a driving current to said electromagnet; and means for controlling the frequency and amplitude of said driving current.

14. An apparatus for vibrating a thin metal plate, comprising an electromagnet having a first and a second end, to be disposed a distance from the surface of said thin metal plate, the ends of said electromagnet having a concave surface;

a pair of rare earth permanent magnets, each of said permanent magnets fixedly disposed at each concave end of said electromagnet;

means for supplying a driving current to said electromagnet; and means for controlling the frequency and amplitude of said driving current.

15. A method for high speed monitoring of fatigue cracks in a thin plate, comprising the steps of:

(a) producing resonant vibrations in said thin plate by actuating a non-contacting vibrating source which generates a sinusoidal driving function;

(b) detecting the resonance frequency of said thin plate; and (c) determining fatigue crack size in said thin plate by correlating the resonance frequency of said thin plate to resonance frequencies associated with known crack sizes of a thin plate of similar dimensions and composition.

16. The method of monitoring fatigue cracks of claim 15 wherein said actuation of non-contacting vibrating source further comprises the steps of:

(a) attaching a pair of permanent magnets to said thin plate whereby the area of said thin plate to be monitored lies between said pair of permanent magnets, the poles of each permanent magnet aligned such that forces on opposite sides of said thin plate are in opposite directions;

(b) disposing two electromagnets at a distance from the permanent magnets and the surface of said thin plate, the first electromagnet disposed directly above said permanent magnets, and the second electromagnet disposed directly below said permanent magnets such that oppositely charged poles of said electromagnets align with each other and align with an associated permanent magnet along an axis;

(c) supplying a sinusoidal driving current to said electromagnets; and (d) controlling the frequency and amplitude of said driving current.

17. The method of monitoring fatigue cracks of claim 16 wherein said detecting of the resonance frequency of said thin plate further comprises the steps of:

(a) detecting stress waves in said thin plate resulting from the produced resonant vibrations by disposing a transducer on the surface of said thin plate, said transducer outputting voltages proportional to the amplitude of said stress waves; and (b) tracking the peak output voltages from said transducer; and (c) correlating said peak output voltages with crack length.

18. A method for high speed monitoring of fatigue cracks in a thin plate, comprising the steps of:

(a) producing resonant vibrations in said thin plate by actuating vibrating source which generates a sinusoidal driving function;

(b) detecting acoustic emissions produced by the interactions of crack faces resulting from resonant vibration of said thin plate; and (c) characterizing the geometry of a crack in said thin plate by correlating detected acoustic emissions from said thin plate to acoustic emissions obtained from cracks with known geometries in thin plates of similar dimensions and composition.

19. The method of monitoring fatigue cracks of claim 18 wherein actuation of said vibrating source further comprises the steps of:

(a) attaching a pair of permanent magnets to said thin plate whereby the area of said plate to be monitored lies between said pair of permanent magnets, the poles of each magnet aligned such that forces on opposite sides of said thin plate are in opposite directions; and (b) disposing two electromagnets at a distance from the permanent magnets and the surface of said thin plate, the first electromagnet disposed directly above said permanent magnets, and the second electromagnet disposed directly below said permanent magnets such that oppositely charged poles of said electromagnets align with each other and align with an associated permanent magnet along an axis.

(c) supplying a sinusoidal driving current to said electromagnets; and (d) controlling the frequency and amplitude of said driving current.

20. The method of monitoring fatigue cracks of claim 18 wherein said vibrating source comprises a pair of rare earth permanent magnets, each of said rare earth permanent magnets fixedly attached to each end of an electromagnet, the surface of each end of said electromagnet having a concave curvature and the surface of said rare earth permanent magnets having a convex curvature, actuation of said vibrating source further comprising the steps of:

(a) disposing said electromagnet and rare earth permanent magnets at a distance from the surface of said thin plate;

(b) supplying a sinusoidal driving current to said electromagnets; and (c) controlling the frequency and amplitude of said driving current.

21. A method -for high speed monitoring of fatigue cracks in a thin plate, comprising the steps of:

(a) producing resonant vibrations in said thin plate by actuating a non-contacting vibrating source which generates a sinusoidal driving function;

(b) detecting the resonance frequency of said thin plate; and (c) determining fatigue crack size in said thin plate by correlating the resonance frequency of said thin plate to resonance frequencies associated with known crack sizes calculated by finite element modeling of a thin plate of similar dimensions and composition.

(d) detecting acoustic emissions produced by the interactions of crack faces resulting from resonant vibrations of said thin plate; and (e) characterizing the geometry of a crack in said thin plate by correlating acoustic emissions from said thin plate to acoustic emissions obtained from cracks with known geometries in thin plates of similar dimensions and composition.

22. The method of monitoring fatigue cracks of claim 21 wherein said actuation of vibrating source further comprises the steps of:

(a) attaching a pair of permanent magnets to said thin plate whereby the area of said thin plate to be monitored lies between said pair of permanent magnets, the poles of each magnet aligned such that forces on opposite sides of said thin plate are in opposite directions; and (b) disposing two electromagnets at a distance from the permanent magnets and the surface of said thin plate, the first electromagnet disposed directly above said permanent magnets, and the second electromagnet disposed directly below said permanent magnets such that oppositely charged poles of said electromagnets align with each other and align with an associated permanent magnet along an axis.

(c) supplying a sinusoidal driving current to said electromagnets; and (d) controlling the frequency and amplitude of said driving current.

23. The method of monitoring fatigue cracks of claim 21 wherein said vibrating source comprises a pair of rare earth permanent magnets, each of said rare earth permanent magnets fixedly attached to each end of an electromagnet, each end of said electromagnet having a concave curvature and the surface of said rare earth permanent magnets having a convex curvature, actuation of said vibrating source further comprising the steps of:

(a) disposing said electromagnet and rare earth permanent magnets at a distance from the surface of said thin plate;

(b) supplying a sinusoidal driving current to said electromagnets; and (c) controlling the frequency and amplitude of said driving current.

24. The method of monitoring fatigue cracks of claim 21 wherein said recording of the resonance frequency of said thin plate further comprises the steps of:

(a) detecting stress waves in said thin plate resulting from the produced resonant vibrations by disposing a transducer on the surface of said thin plate, said transducer outputting voltages proportional to the amplitude of said stress waves;

(b) tracking the peak output voltages from said transducer; and (c) correlating said peak output voltages with crack length.

25. An apparatus for high speed monitoring of fatigue cracks in a thin plate, comprising:

a vibrator for vibrating said thin plate to produce resonant vibrations by generating a sinusoidal driving function, wherein said vibrator does not contact said thin plate, the vibrator having:

an electromagnet having a first and a second end, to be disposed a distance from the surface of said thin plate, the ends of said electromagnet having a concave surface;

a pair of rare earth permanent magnets, each of said permanent magnets fixedly disposed at each concave end of said electromagnet;

means for supplying a driving current to said electromagnet;

means for controlling the frequency and amplitude of said driving current; and means for detecting resonance frequency shifts resulting from cracks in said thin plate, wherein said resonance frequency shifts are correlated to crack length.

* * * * *